US012587845B2

(12) United States Patent
Kasahara et al.

(10) Patent No.: US 12,587,845 B2
(45) Date of Patent: Mar. 24, 2026

(54) ULTRASONIC DIAGNOSTIC APPARATUS

(71) Applicant: FUJIFILM Healthcare Corporation,
Kashiwa (JP)

(72) Inventors: Eiji Kasahara, Chiba (JP); Koji Waki,
Chiba (JP); Akira Kusakabe, Chiba
(JP); Suguru Ishiguro, Chiba (JP)

(73) Assignee: FUJIFILM Corporation, Tokyo (JP)

( * ) Notice: Subject to any disclaimer, the term of this
patent is extended or adjusted under 35
U.S.C. 154(b) by 227 days.

(21) Appl. No.: 18/213,370

(22) Filed: Jun. 23, 2023

(65) Prior Publication Data

US 2024/0007854 A1 Jan. 4, 2024

(51) Int. Cl.
*H04W 12/06* (2021.01)
*A61B 8/00* (2006.01)
*H04N 7/18* (2006.01)

(52) U.S. Cl.
CPC ........... *H04W 12/06* (2013.01); *A61B 8/4472*
(2013.01); *A61B 8/565* (2013.01); *H04N*
*7/183* (2013.01)

(58) Field of Classification Search
CPC ...... H04W 12/06; A61B 8/4472; A61B 8/565;
A61B 8/465; A61B 8/54; H04N 7/183
USPC ........................................................ 382/306
See application file for complete search history.

(56) References Cited

U.S. PATENT DOCUMENTS

2012/0101389 A1* 4/2012 Tanabe ................. A61B 8/4438
600/459
2013/0184587 A1* 7/2013 Eom ...................... A61B 8/565
600/443

FOREIGN PATENT DOCUMENTS

JP 2000-175870 A 6/2000
JP 2008-104595 A 5/2008
JP 2011-072583 A 4/2011

OTHER PUBLICATIONS

Feb. 17, 2026 Japanese official action (and machine translation in
English thereof) in connection with Japanese Patent Application No.
2022-107151.

* cited by examiner

*Primary Examiner* — Neil R Mclean
(74) *Attorney, Agent, or Firm* — Paul Teng

(57) ABSTRACT

An ultrasonic diagnostic apparatus includes a wireless com-
munication unit and a control unit. The wireless communi-
cation unit is connected to a communication line via a
wireless relay device, communicates with an information
terminal via the communication line, and transmits ultra-
sonic image information to the information terminal. The
control unit selects a shared group ID, which is one of a
plurality of registered group IDs registered in advance,
according to an operation of a user. The control unit,
together with the wireless communication unit, transmits the
shared group ID to the wireless relay device. The wireless
relay device receives an affiliated group ID from the infor-
mation terminal to establish wireless communication with
the information terminal for which the affiliated group ID
matching the shared group ID is received.

8 Claims, 8 Drawing Sheets

ULTRASONIC DIAGNOSTIC APPARATUS

CROSS REFERENCE TO RELATED APPLICATION

This application claims priority to Japanese Patent Application No. 2022-107151 filed on Jul. 1, 2022, which is incorporated herein by reference in its entirety including the specification, claims, drawings, and abstract.

TECHNICAL FIELD

The present disclosure relates to an ultrasonic diagnostic apparatus, and more particularly, to an apparatus which transmits ultrasonic image information to an information terminal.

BACKGROUND

Research and development have been conducted on an ultrasonic diagnostic system which transmits ultrasonic image information generated by an ultrasonic diagnostic apparatus, via a wireless local area network (LAN), to an information terminal such as a tablet or a smartphone and causes the information terminal to display an ultrasonic image. Some ultrasonic diagnostic systems ensure security of communication between an ultrasonic diagnostic apparatus and an information terminal by the information terminal collating security information with the ultrasonic diagnostic apparatus. For example, the information terminal transmits a collation signal including specific security information to an access point of a wireless LAN, and when the security information in the collation signal is set in the access point, the access point establishes communication between the information terminal and the ultrasonic diagnostic apparatus.

Patent Literature 1 below discloses an ultrasonic diagnostic system in which wireless communication is performed between an ultrasonic probe and an ultrasonic observation device as a technique related to the present disclosure. The ultrasonic observation device determines whether wireless communication with the ultrasonic probe can be established based on authentication information transmitted from the ultrasonic probe. Patent Literature 2 discloses a medical image diagnostic system in which an ultrasonic probe and each main body of a plurality of ultrasonic diagnostic apparatuses are wirelessly connected.

CITATION LIST

PATENT LITERATURE

PATENT LITERATURE 1: JP 2011-72583 A
PATENT LITERATURE 2: JP 2008-104595 A

SUMMARY

In an ultrasonic diagnostic system in the related art, unchanging security information is set in the wireless LAN, and thus unauthorized access may be made to an ultrasonic diagnostic apparatus. For example, an information terminal owned by a person not related to diagnosis performed by the ultrasonic diagnostic apparatus may access the ultrasonic diagnostic apparatus and acquire an ultrasonic image.

An object of the present disclosure is, for an ultrasonic diagnostic apparatus which transmits ultrasonic image information to information terminals, to prevent unauthorized acquisition of ultrasonic image information by an information terminal.

The present disclosure includes: a wireless communication unit connected to a communication line via a wireless relay device, configured to communicate with an information terminal via the communication line, and configured to transmit ultrasonic image information to the information terminal; and a control unit configured to control the wireless communication unit. The control unit executes group selection processing of selecting a shared group ID, which is one of a plurality of registered group IDs registered in advance, according to an operation of a user, and, together with the wireless communication unit, transmits the shared group ID to the wireless relay device. The wireless relay device receives an affiliated group ID from the information terminal, to establish wireless communication with the information terminal for which the affiliated group ID that matches the shared group ID is received.

In one embodiment, the control unit, together with the wireless communication unit, communicates via the communication line with a plurality of information terminals which transmit the same affiliated group ID to the wireless relay device.

In one embodiment, the control unit determines whether the information terminal, for which the affiliated group ID that does not match the shared group ID is received by the wireless relay device, is an unauthorized access wireless terminal based on a communication operation of the information terminal.

The present disclosure includes: an authentication wireless unit configured to perform wireless communication with an information terminal and transmit ultrasonic image information to the information terminal; and a control unit configured to control the authentication wireless unit. The control unit executes group selection processing of selecting a shared group ID, which is one of a plurality of registered group IDs registered in advance, according to an operation of a user, receives an affiliated group ID from the information terminal together with the authentication wireless unit, and causes the authentication wireless unit to perform wireless communication with the information terminal for which the affiliated group ID matching the shared group ID is received.

In one embodiment, the control unit causes the authentication wireless unit to perform wireless communication with a plurality of information terminals for which the same affiliated group ID is received.

In one embodiment, the control unit determines whether the information terminal, for which the affiliated group ID that does not match the shared group ID is received, is an unauthorized access wireless terminal based on a communication operation of the information terminal.

According to the present disclosure, for the ultrasonic diagnostic apparatus which transmits the ultrasonic image information to the information terminals, it is possible to prevent unauthorized acquisition of the ultrasonic image information by an information terminal.

BRIEF DESCRIPTION OF DRAWINGS

Embodiment(s) of the present disclosure will be described based on the following figures, wherein.

DESCRIPTION OF EMBODIMENTS

Figure 1:
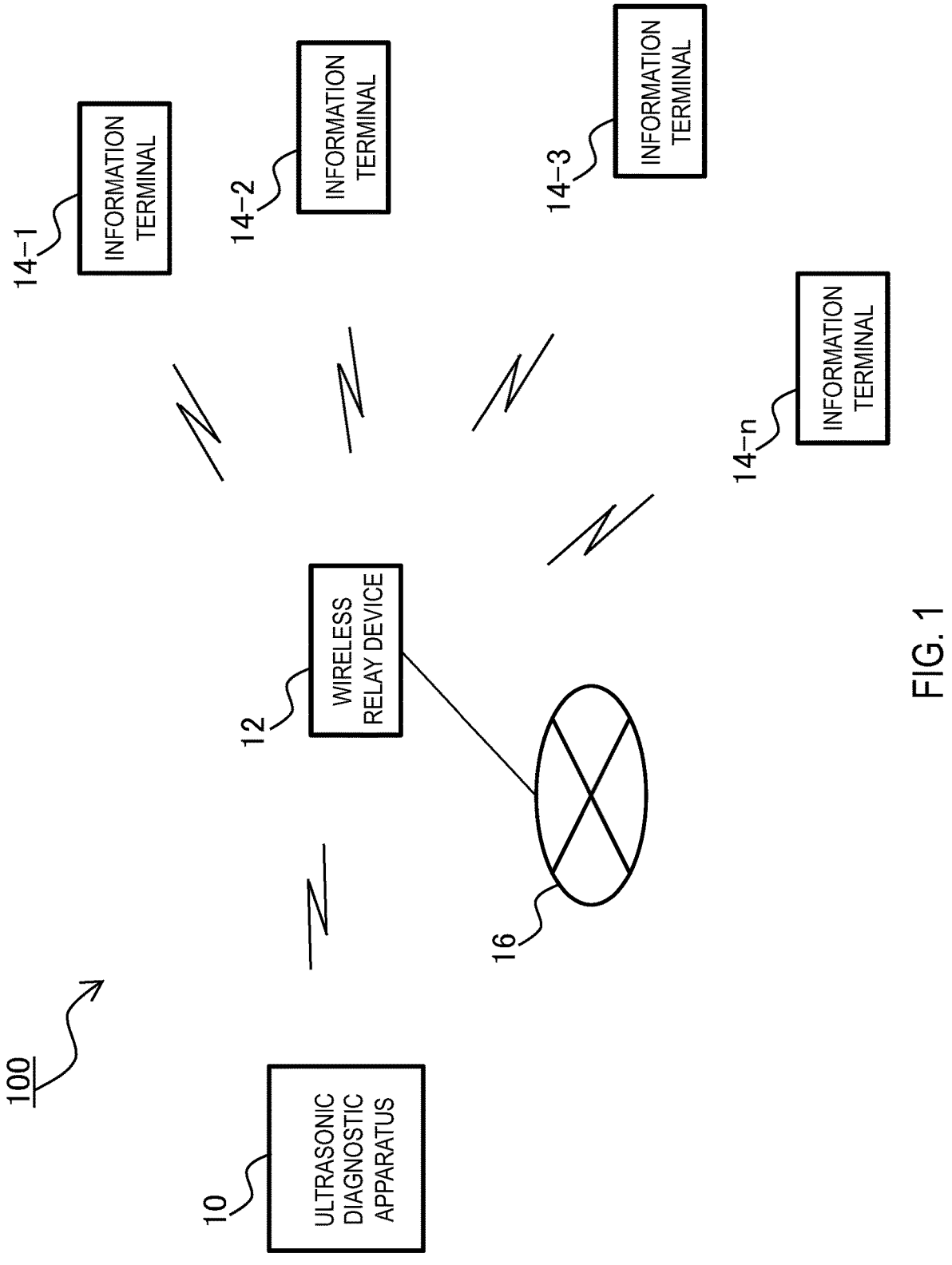
FIG. 1 is a diagram showing a configuration of an ultrasonic diagnostic system according to a first embodiment.

Embodiments according to the present disclosure will be described with reference to drawings. The same components shown in the drawings are denoted by the same reference signs, and description thereof is omitted.

FIG. 1 shows a configuration of an ultrasonic diagnostic system 100 according to a first embodiment of the present disclosure. The ultrasonic diagnostic system 100 includes an ultrasonic diagnostic apparatus 10, a wireless relay device 12, and information terminals 14-1 to 14-$n$ ($n$ is an integer equal to or larger than 1). The wireless relay device 12 is connected to a communication line 16 such as the Internet or the like. As such a wireless relay device, there is an access point conforming to the Wi-Fi (registered trademark) standard or the like. Each of the information terminals 14-1 to 14-$n$ may be a personal computer, a tablet computer, a smartphone, or the like having a wireless communication function. In the following description, a reference sign "14" is used as a reference sign indicating any one of the information terminals 14-1 to 14-$n$.

The ultrasonic diagnostic apparatus 10 and each information terminal 14 are connected to the communication line 16 by wireless communication with the wireless relay device 12. Information is transmitted and received between the ultrasonic diagnostic apparatus 10 and each information terminal 14 via the wireless relay device 12 and the communication line 16. For example, the ultrasonic diagnostic apparatus 10 transmits ultrasonic image data indicating an image obtained by transmitting and receiving ultrasonic waves to and from a subject from the wireless relay device 12 to the communication line 16, and from the communication line 16, via a communication path through the wireless relay device 12, to each information terminal 14. Each information terminal 14 displays an image based on the ultrasonic image data. In the following description, a communication path from the wireless relay device 12 to the communication line 16 and from the communication line 16 through the wireless relay device 12 may be simply referred to as "via the communication line 16".

Figure 2:
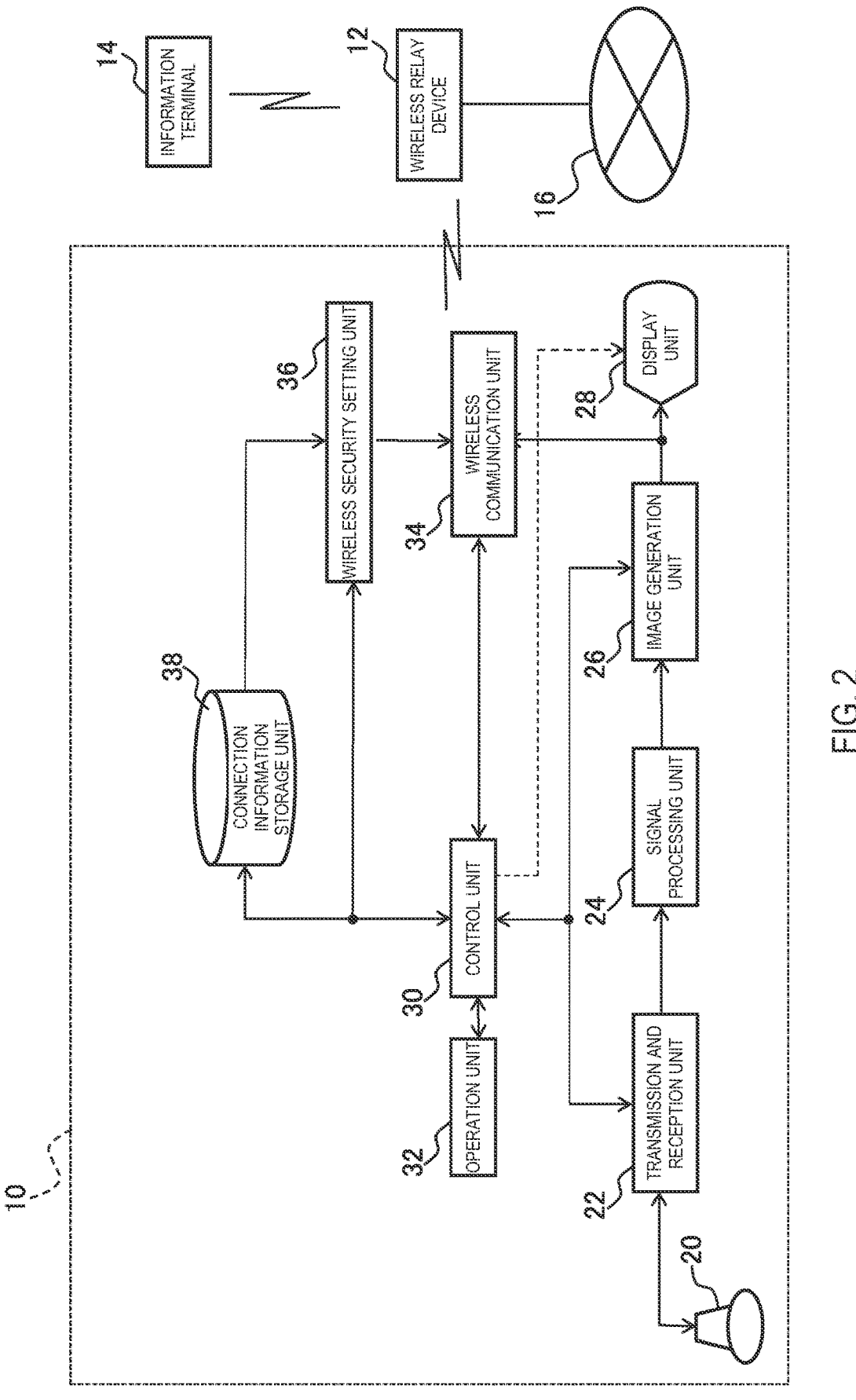
FIG. 2 is a diagram showing a configuration of an ultrasonic diagnostic apparatus according to the first embodiment.

FIG. 2 shows a configuration of the ultrasonic diagnostic apparatus 10. The ultrasonic diagnostic apparatus 10 includes an ultrasonic probe 20, a transmission and reception unit 22, a signal processing unit 24, an image generation unit 26, a display unit 28, a control unit 30, an operation unit 32, a wireless communication unit 34, a wireless security setting unit 36, and a connection information storage unit 38.

The signal processing unit 24, the image generation unit 26, the control unit 30, and the wireless security setting unit 36 may include a processor and an electronic circuit for implementing functions of components of these units (the signal processing unit 24, the image generation unit 26, the control unit 30, and the wireless security setting unit 36) by executing a program. The wireless communication unit 34 includes an electronic circuit for implementing a wireless communication function.

The control unit 30 executes overall control over the ultrasonic diagnostic apparatus 10. The operation unit 32 may include a button, a lever, a keyboard, a mouse, and the like. The operation unit 32 may be a touch panel provided in the display unit 28. The control unit 30 may control the ultrasonic diagnostic apparatus 10 based on an operation by a user of the ultrasonic diagnostic apparatus 10 (hereinafter, referred to as a diagnostic apparatus user). The connection information storage unit 38 stores a database for the wireless communication unit 34 to perform communication.

The ultrasonic probe 20 includes a plurality of ultrasonic transducers. The transmission and reception unit 22 outputs transmitted signals, which are electrical signals, to the plurality of ultrasonic transducers. Each ultrasonic transducer converts a transmitted signal into an ultrasonic wave and transmits the ultrasonic wave to the subject. The transmission and reception unit 22 adjusts a delay time of a transmitted signal output to each ultrasonic transducer, thereby forming an ultrasonic beam in a specific direction.

The ultrasonic transducer receives an ultrasonic wave reflected in the subject, converts the ultrasonic wave into a received signal which is an electrical signal, and outputs the received signal to the signal processing unit 24. The signal processing unit 24 adjusts a delay time of a received signal output from each ultrasonic transducer and sums each received signal after the delay time adjustment, such that received signals due to the ultrasonic waves arriving from a direction to which an ultrasonic beam is directed strengthen each other. The signal processing unit 24 outputs a delay-and-sum signal generated in this manner to the image generation unit 26.

The transmission and reception unit 22 changes a delay time of a transmitted signal output to each ultrasonic transducer so that the subject is scanned with an ultrasonic beam in a specific observation cross section. The signal processing unit 24 changes a delay time of a received signal output from each ultrasonic transducer and sums each received signal after the delay time adjustment, so as to generate a phased-and-summed signal corresponding to a direction of the ultrasonic beam with which the subject is scanned.

The image generation unit 26 generates B-mode image data based on the phased-and-summed signal acquired in each direction in the observation cross section. The transmission and reception unit 22, the signal processing unit 24, and the image generation unit 26 sequentially generate B-mode image data at a predetermined frame rate with elapse of time. Here, the frame rate refers to the number of B-mode images generated per unit time.

The image generation unit 26 generates a video signal based on the B-mode image data sequentially generated with elapse of time, and outputs the video signal to the display unit 28. The display unit 28 may be a display device which displays information on an image, text data, or the like. The display unit 28 displays, based on the video signal, an image based on the B-mode image data sequentially generated with elapse of time, that is, a real-time image of the B-mode image.

In the above description, processing of scanning with the ultrasonic beam in the subject and generating the B-mode image based on the phased-and-summed signal corresponding to an ultrasonic beam in each direction is shown. The ultrasonic diagnostic apparatus 10 may execute an operation in a Doppler mode for obtaining a velocity of a blood flow based on a difference in frequency of the phased-and-summed signal relative to a frequency of a transmitted signal (Doppler shift). For example, the signal processing unit 24 generates Doppler data representing the velocity of the blood flow in a predetermined range (Doppler gate) defined on the ultrasonic beam in each direction, and outputs the Doppler data to the image generation unit 26. The image generation unit 26 may generate a video signal indicating a Doppler image in which an image indicating the velocity of the blood flow is superimposed on the B-mode image, and output the video signal to the display unit 28. The display unit 28 displays the Doppler image.

The wireless communication unit 34 performs wireless communication with the wireless relay device 12 and is communicably connected, via the wireless relay device 12, to the communication line 16. The wireless communication unit 34 communicates with the information terminal 14 via the communication line 16. Before the wireless communication unit 34 starts communication with the information terminal 14, the following communication connection processing is performed.

The wireless communication unit 34 sets a communicator ID and security information for the wireless relay device 12 by wireless communication with the wireless relay device 12. The communicator ID is an identification (ID) for identifying the wireless relay device 12. The security information is a code for establishing wireless communication with the wireless relay device 12. Here, a state in which the wireless communication is established refers to, for example, a state in which a plurality of communication devices can communicate using the same communication protocol.

When the wireless relay device 12 is a Wi-Fi access point, the communicator ID and the security information are a service set identifier (SSID) and a security key, respectively. For example, the wireless security setting unit 36 reads a communicator ID from the connection information storage unit 38, and acquires from the control unit 30 the security information read from the operation unit 32 to the control unit 30. The wireless security setting unit 36 outputs the communicator ID and the security information to the wireless communication unit 34. The wireless communication unit 34 transmits a setting signal including the communicator ID and the security information to the wireless relay device 12, and sets the communicator ID of and the security information on the wireless relay device 12. The wireless communication unit 34 establishes wireless communication with the wireless relay device 12 using the communicator ID and the security information set for the wireless relay device 12. Accordingly, the wireless communication unit 34 is communicably connected to the communication line 16.

Figure 3:
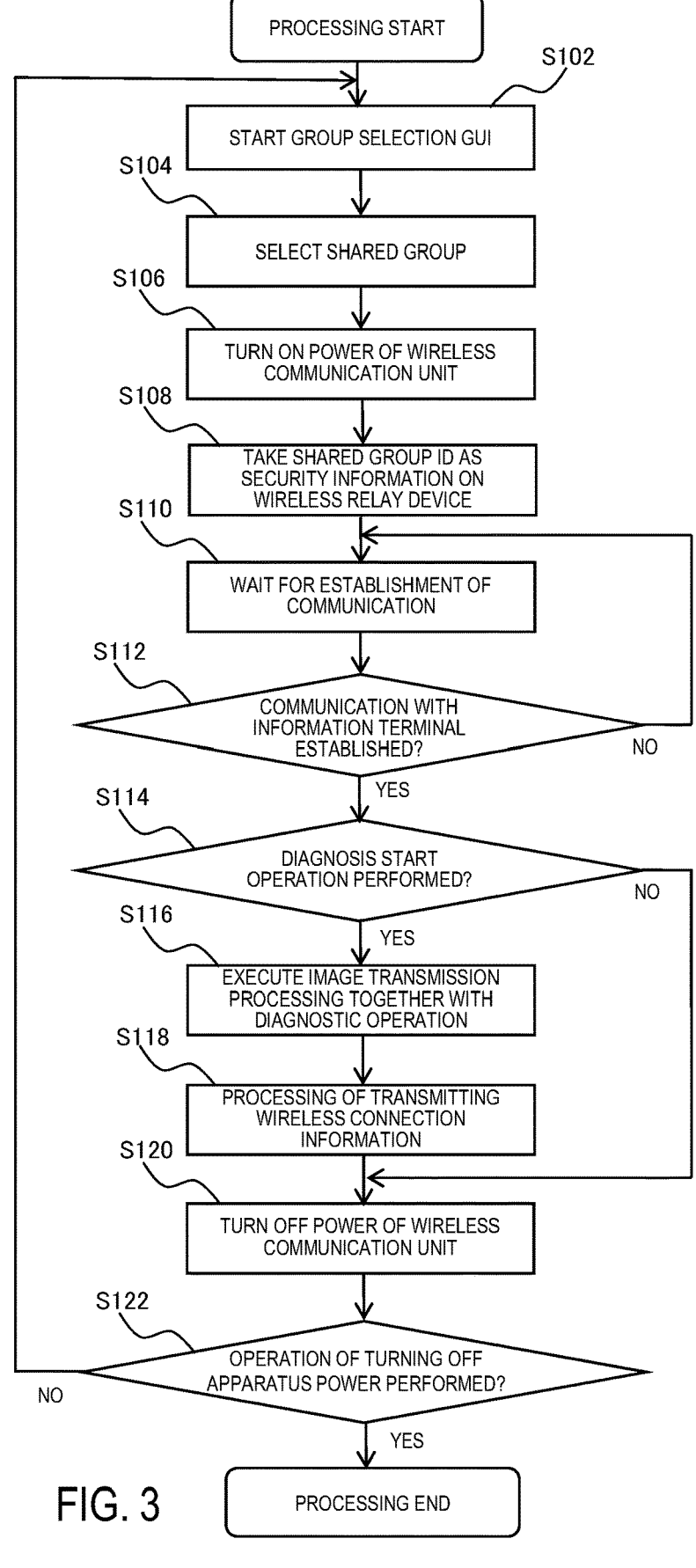
FIG. 3 is a flowchart of processing executed by the ultrasonic diagnostic apparatus according to the first embodiment.

An operation example of the ultrasonic diagnostic apparatus 10 will be described. FIG. 3 shows a flowchart of processing executed by the ultrasonic diagnostic apparatus 10 according to the present embodiment. In an initial state, power of the ultrasonic diagnostic apparatus 10 is on, but power of the wireless communication unit 34 is off. A certain code is set as the communicator ID in the wireless relay device 12.

In accordance with an operation of the operation unit 32 by the diagnostic apparatus user, the control unit 30 starts a group selection graphical user interface (GUI) (S102). Here, the group selection GUI is a GUI for allowing a user to select one group from a plurality of registered groups. Each of the plurality of registered groups is formed by one or a plurality of information terminals 14. A registered group identification (ID) for identifying a registered group is registered in the ultrasonic diagnostic apparatus 10 in advance. A state in which the registered group ID is registered may be a state in which the registered group ID is stored in the connection information storage unit 38. When the control unit 30 can transmit and receive, via the wireless communication unit 34, information to and from an external computer connected to the communication line 16, the state in which the registered group ID is registered may be a state in which the registered group ID is stored in the external computer.

By processing to be described later, only the information terminal 14 belonging to the group selected by the group selection GUI is allowed to communicate with the wireless communication unit 34 via the communication line 16. That is, only the information terminal 14 whose affiliated group ID (belonging group ID) matches a shared group ID, which is the registered group ID selected by the group selection GUI, is allowed to communicate with the wireless communication unit 34 via the communication line 16.

Figure 4:
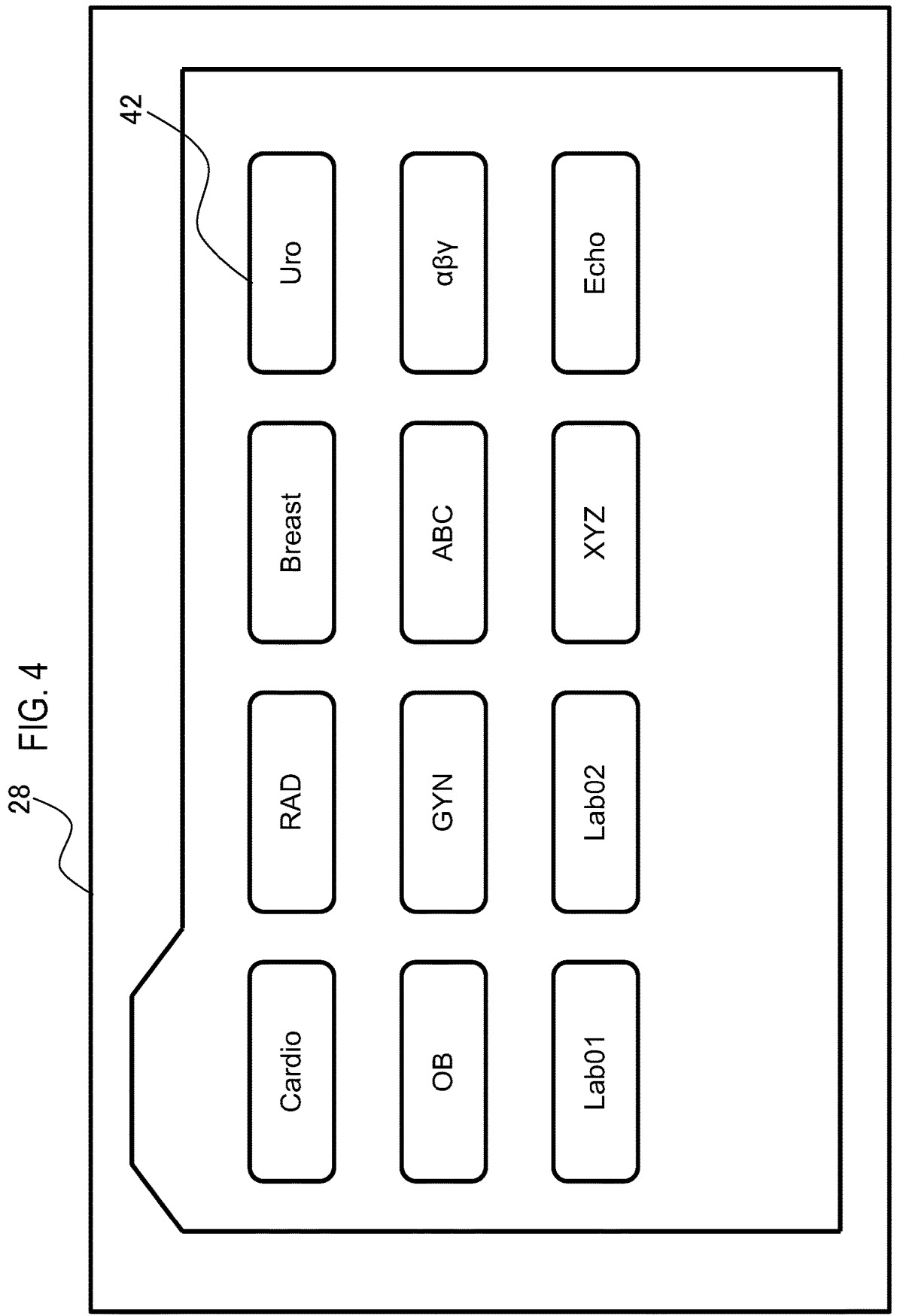
FIG. 4 is a diagram showing an operation image displayed on a display unit.

FIG. 4 shows an operation image displayed on the display unit 28 by the control unit 30 when the group selection GUI is started. In the operation image shown in FIG. 4, 12 buttons marked with "Cardio", "RAD", "Breast", "Uro" . . . are shown as names of the registered groups. In this example, there are 12 registered groups which are registered in advance and can be selected as the shared group.

When the operation image is displayed on the display unit 28, the user selects a shared group (S104). When the display unit 28 is a touch panel, a registered group corresponding to a button 42 is selected by touching the button 42 with a finger of the user of the ultrasonic diagnostic apparatus 10. When the display unit 28 is a normal display, a registered group corresponding to the button 42 is selected by pressing the button 42 with a cursor or the like.

The control unit 30 reads, from the connection information storage unit 38, the registered group ID corresponding to the button pressed by an operation of the user as the shared group ID.

The control unit 30 turns on the power of the wireless communication unit 34 (S106), and outputs the shared group ID to the wireless security setting unit 36. The wireless security setting unit 36 outputs the shared group ID as the security information to the wireless communication unit 34. The wireless communication unit 34 transmits a setting signal including the shared group ID to the wireless relay device 12 in accordance with control of the control unit 30, and takes the shared group ID as the security information on the wireless relay device 12 (S108). Accordingly, the wireless communication unit 34 enters a state of waiting for establishment of communication with the information terminal 14 via the communication line 16 (S110).

The information terminal 14 belongs to any one of a plurality of registered groups. The registered group may be formed, for example, for each research organization related to a specific site of a patient or for each department in a hospital. The registered group may be formed for each research team in a research institution such as a university. For example, when a user of the information terminal 14 (hereinafter, referred to as a terminal user) belongs to a research organization related to circulatory organs, the information terminal 14 may belong to a registered group formed in the research organization related to circulatory organs (circulatory organ registered group). The information terminal 14 is assigned an affiliated group ID given in advance to the circulatory organ registered group. The terminal user is notified of the communicator ID for the information terminal 14 to perform communication connection with the ultrasonic diagnostic apparatus 10 from the research organization to which the terminal user belongs.

The terminal user inputs the communicator ID and the affiliated group ID to the information terminal 14. The information terminal 14 reads the communicator ID and the affiliated group ID according to an operation of the terminal user, and sets the communicator ID and the affiliated group ID as a collation communicator ID and collation security information, respectively. The information terminal 14 transmits a collation signal including the collation communicator ID and the collation security information to the wireless relay device 12.

The wireless relay device 12 receives a collation signal and extracts the collation communicator ID and the collation security information from the collation signal. The wireless relay device 12 determines whether the collation communicator ID and the collation security information (affiliated group ID) match the communicator ID and the security information (shared group ID) set in the wireless relay device 12, respectively. When the collation communicator ID and the collation security information (affiliated group ID) match the communicator ID and the security information (shared group ID), respectively, the wireless relay device 12 establishes wireless communication with the information terminal 14 and also establishes communication between the information terminal 14 and the ultrasonic diagnostic apparatus 10 via the communication line 16.

When the collation communicator ID does not match the communicator ID or the collation security information (affiliated group ID) does not match the security information (shared group ID), the wireless relay device 12 does not establish wireless communication with the information terminal 14. Accordingly, communication between the information terminal 14 and the ultrasonic diagnostic apparatus 10 via the communication line 16 is not to be established.

Processing in step S112 and following steps in FIG. 3 will be described. The control unit 30 determines whether communication between the wireless communication unit 34 and the information terminal 14 is established (S112), and if the communication is not established waits for establishment of the communication between the wireless communication unit 34 and the information terminal 14 (S110). When it is determined that the communication between the wireless communication unit 34 and the information terminal 14 is established, the control unit 30 determines whether a diagnosis start operation is performed (S114).

When the diagnosis start operation is performed, the control unit 30 starts a diagnostic operation (S116). As described above, the diagnostic operation refers to an operation in which the signal processing unit 24 generates B-mode image data, Doppler data, and the like, and the display unit 28 displays an ultrasonic image such as a B-mode image, and a Doppler image. On the other hand, when the diagnosis start operation is not performed, the control unit 30 proceeds to processing of step S120, to be described later.

The control unit 30 executes image transmission processing together with the diagnostic operation (S116). The image transmission processing is processing of transmitting ultrasonic image information to the information terminal 14. The ultrasonic image information may be information including ultrasonic image data generated by the image generation unit 26 or a video signal based on the ultrasonic image data.

The information terminal 14 receives ultrasonic image information transmitted from the wireless communication unit 34 via the communication line 16, and displays an ultrasonic image based on the ultrasonic image information.

The control unit 30 transmits the wireless connection information (S118). Here, the wireless connection information refers to information indicating one or more information terminals 14 which establish communication with the ultrasonic diagnostic apparatus 10.

The wireless connection information may include unauthorized access information indicating that there is a wireless terminal which attempts unauthorized access to the wireless relay device 12. The unauthorized access information may be information indicating the number of wireless terminals which attempt unauthorized access. The control unit 30 performs wireless communication with the wireless relay device 12 via the wireless communication unit 34, and acquires, for example, information on whether there is a wireless terminal for which authentication has not been successful for a predetermined N times or more. Alternatively, the control unit 30 acquires the number of such unauthorized access wireless terminals from the wireless relay device 12. That is, the control unit 30 acquires information on whether there is an unauthorized access wireless terminal which transmits a collation signal such that the collation communicator ID does not match the communicator ID or the collation security information (affiliated group ID) does not match the security information (shared group ID) N times or more. Alternatively, the control unit 30 acquires the number of unauthorized access wireless terminals. N may be a numerical value exceeding a number of acceptable operation errors or the like.

The unauthorized access information may include information recording a communication operation in which authentication is not successful for a predetermined N times or more, and other communication operations. For example, the unauthorized access information may include information recording a communication operation specified by a frequency of reception of a collation signal which is not successfully authenticated (the number of times the collation signal is received per unit time), a pattern in which information in the collation signal transmitted a plurality of times changes, or the like.

In the processing of step S118, the control unit 30 transmits wireless connection information to the information terminal 14 via the wireless communication unit 34. The wireless connection information may be displayed together with the ultrasonic image by the information terminal 14.

Thus, the control unit 30 executes group selection processing of selecting a shared group ID, which is one of a plurality of registered group IDs registered in advance, in accordance with an operation of the user (S102, S104). When an affiliated group ID the same as the shared group ID is in the collation signal transmitted from the information terminal 14 to the wireless relay device 12, the control unit 30 executes the image transmission processing together with the wireless communication unit 34 (S116), and executes processing of transmitting wireless connection information (hereinafter, referred to as connection information transmission processing) (S118).

The control unit 30, together with the wireless communication unit 34, may communicate, via the communication line 16, with the plurality of information terminals 14 which transmit the same affiliated group ID to the wireless relay device 12. In this case, the control unit 30, together with the wireless communication unit 34, executes the image transmission processing for the plurality of information terminals 14 (S116), and executes the connection information transmission processing (S118).

Figure 5:
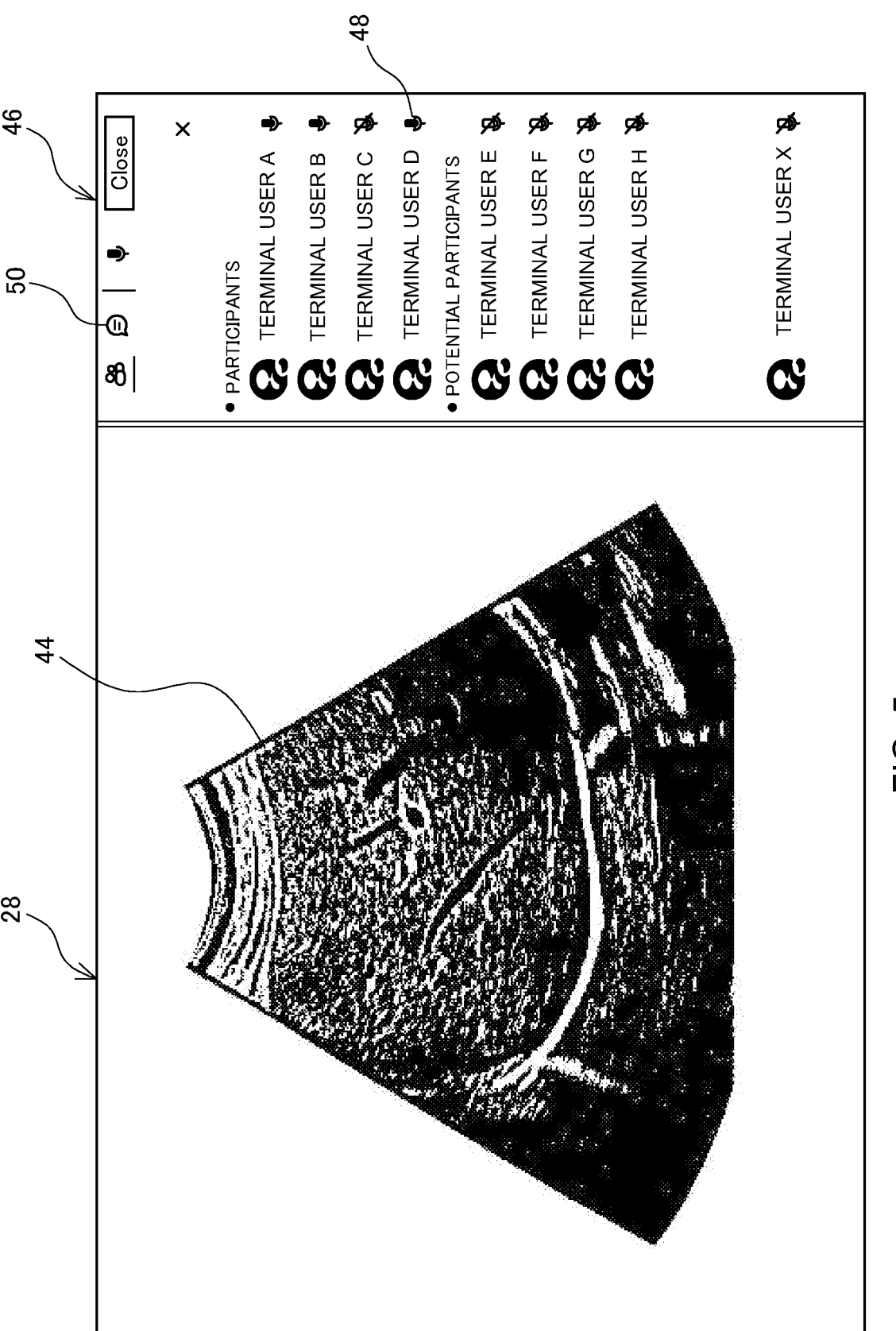
FIG. 5 is a diagram showing an example of an ultrasonic image and wireless connection information displayed on an information terminal.

The image transmission processing and the connection information transmission processing may be performed by a conference system using the communication line 16. The conference system using the communication line 16 includes a web conference system such as Zoom and Teams. FIG. 5 shows an example of an ultrasonic image 44 and wireless connection information 46 displayed on the information terminal 14 which starts the conference system. FIG. 5 shows a B-mode image as the ultrasonic image 44. The wireless connection information 46 is shown to the right of the ultrasonic image 44. The wireless connection information 46 shown in FIG. 5 indicates that information terminals A to H used by terminal users A to H belong to the same registered group. The terminal users A to D are displayed as "participants", and it is shown that the information terminals A to D establish communication with the ultrasonic diagnostic apparatus 10. The terminal users E to H are displayed as "potential participants". That is, it is shown that the information terminals E to H do not establish communication with the ultrasonic diagnostic apparatus 10 at a current time point, but may establish communication in the future. Further, presence of one unauthorized access wireless terminal is displayed as a terminal user X. A graphic 48 indicating a voice connection status in the web conference system and a button 50 for starting a chat are displayed on the display unit 28.

Returning to FIG. 3, further description will be given. After the diagnostic operation ends and the image transmission processing and the connection information transmission processing is executed, the control unit 30 turns off the power of the wireless communication unit 34 (S120). The control unit 30 determines whether an operation of turning off the power (apparatus power) of the ultrasonic diagnostic apparatus 10 is performed (S122). When the operation of turning off the apparatus power is not performed, the control unit 30 returns to the processing of step S102. When the operation of turning off the apparatus power is performed, the control unit 30 ends the processing.

In step S102, the control unit 30 starts the group selection GUI again. In response to an operation of the operation unit 32 by the diagnostic apparatus user, the control unit 30 selects a next shared group ID (S104). In processing in step S102 and following steps, a similar operation to the processing executed for the previous shared group ID is also executed for the next shared group ID.

According to the processing of step S108, the shared group ID is set as the security information on the wireless relay device 12. Therefore, the wireless relay device 12 establishes wireless communication with the information terminal 14 which transmits the collation signal, including the affiliated group ID that is the same as the shared group ID, as the collation security information. The affiliated group ID as the collation security information is read into the information terminal 14 by an operation of a terminal user. Therefore, the ultrasonic image information and the wireless connection information are transmitted to the information terminal 14 possessed by the terminal user who knows the affiliated group ID thereof. Further, the shared group ID is updated every time step S104 is executed. Therefore, unauthorized access by a person who is not related to the shared group is avoided, and confidentiality when transmitting ultrasonic image information and wireless connection information from the ultrasonic diagnostic apparatus 10 to the information terminal 14 is enhanced.

The power of the wireless communication unit 34 is turned on while the processing for one selection of the shared group (S106 to S118) is executed, and is turned off from when the processing for one selection of the shared group ends to when a next shared group is selected. Accordingly, the possibility of unauthorized access to the ultrasonic diagnostic apparatus 10 is reduced.

In the processing shown in FIG. 3, a shared group is selected from a plurality of registered groups by an operation of the diagnostic apparatus user, and security information is set in the shared group ID. In addition to such processing, the ultrasonic diagnostic apparatus 10 may execute processing of setting the communicator ID of the wireless relay device 12 by an operation of the diagnostic apparatus user. In this case, the control unit 30 reads the communicator ID from the operation unit 32 according to the operation of the diagnostic apparatus user. The control unit 30 outputs the communicator ID and the shared group ID to the wireless security setting unit 36. The wireless security setting unit 36 outputs the communicator ID and the shared group ID to the wireless communication unit 34. The wireless communication unit 34 transmits a setting signal including the communicator ID and the shared group ID to the wireless relay device 12 in accordance with control of the control unit 30, sets the communicator ID of the wireless relay device 12, and sets the security information as the shared group ID.

The terminal user is notified of the communicator ID and the affiliated group ID by a research organization to which the terminal user belongs. The terminal user inputs the communicator ID and the affiliated group ID to the information terminal 14. The information terminal 14 reads the communicator ID and the affiliated group ID according to an operation of the terminal user, and sets the communicator ID and the affiliated group ID as a collation communicator ID and collation security information, respectively.

The information terminal 14 transmits a collation signal including the collation communicator ID and the collation security information to the wireless relay device 12. When the collation communicator ID and the collation security information (affiliated group ID) match the communicator ID and the security information (shared group ID) set by the ultrasonic diagnostic apparatus 10, respectively, the wireless relay device 12 establishes wireless communication with the information terminal 14. When the wireless communication between the wireless relay device 12 and the information terminal 14 is established, the information terminal 14 is communicably connected to the communication line 16.

According to such processing, not only the shared group ID but also the communicator ID is changed as needed, rather than being unchanged information. Accordingly, confidentiality when transmitting the ultrasonic image information and the wireless connection information to the information terminal 14 is enhanced.

Figure 6:
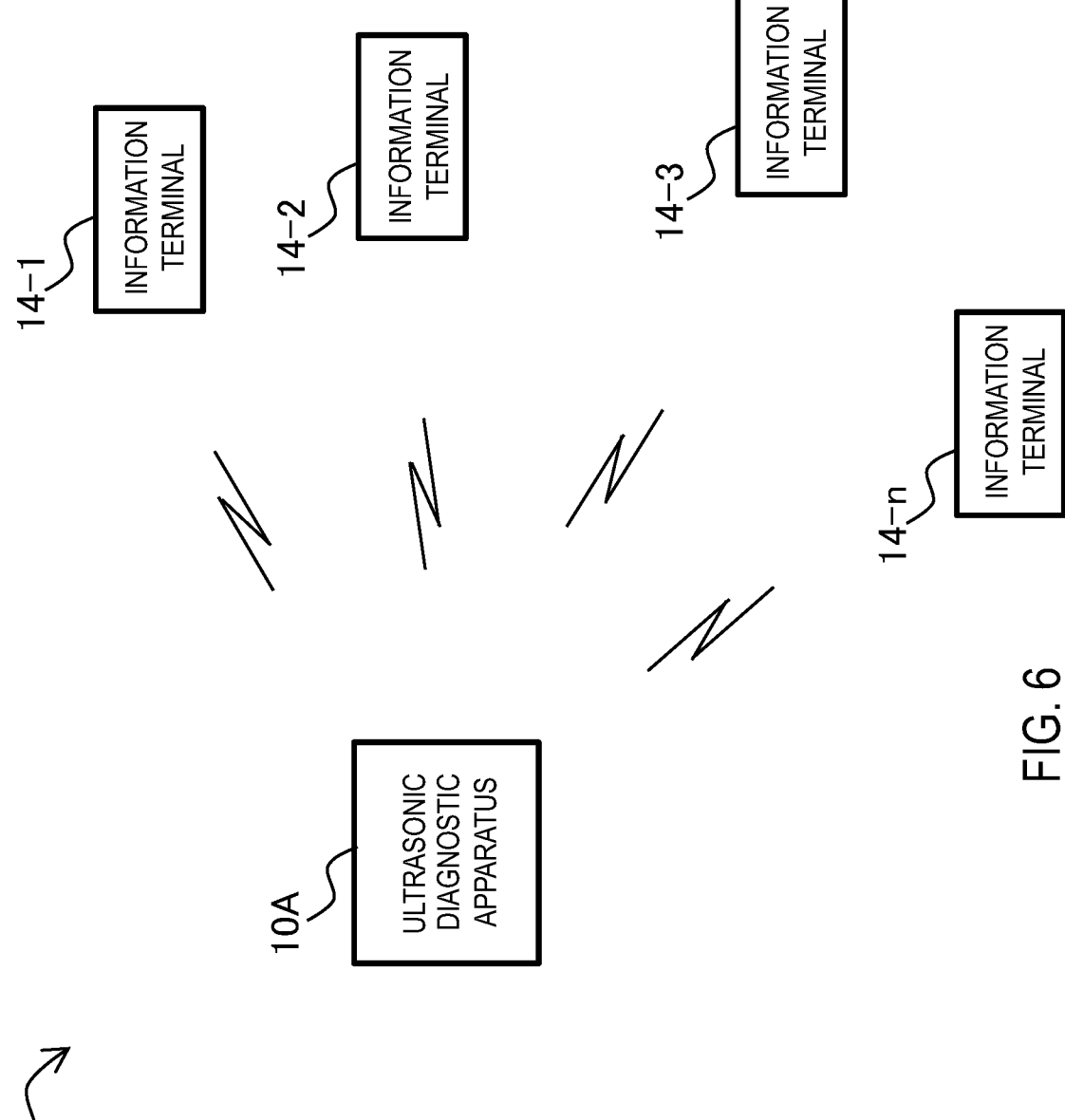
FIG. 6 is a diagram showing a configuration of an ultrasonic diagnostic system according to a second embodiment.

FIG. 6 shows a configuration of an ultrasonic diagnostic system 102 according to a second embodiment of the present disclosure. In the ultrasonic diagnostic system 102, the wireless relay device 12 is not used as in the ultrasonic diagnostic system 100 shown in FIG. 1, and an ultrasonic diagnostic apparatus 10A directly performs wireless communication with each of the information terminals 14-1 to 14-n.

Figure 7:
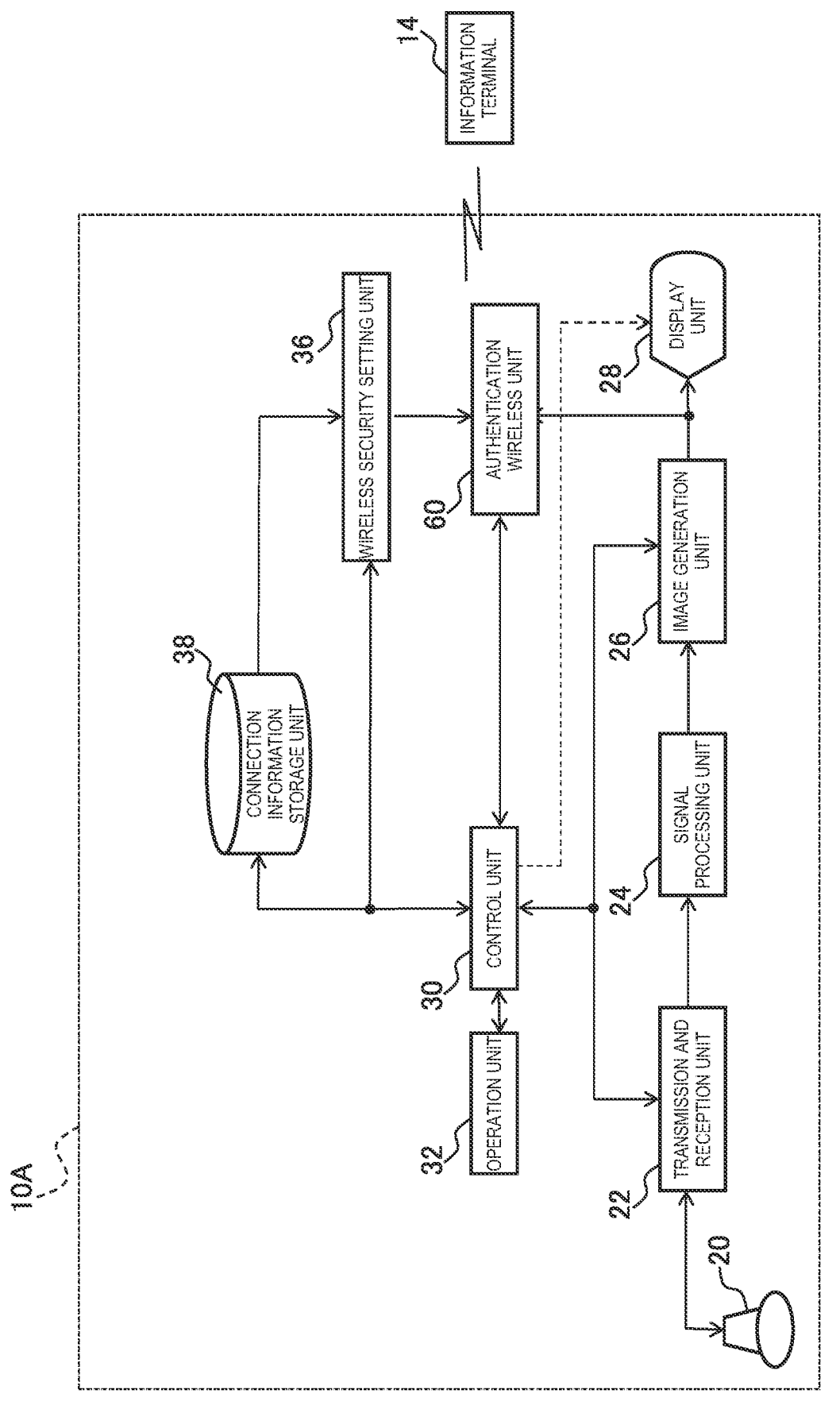
FIG. 7 is a diagram showing a configuration of an ultrasonic diagnostic apparatus according to the second embodiment.

FIG. 7 shows a configuration of the ultrasonic diagnostic apparatus 10A. In the ultrasonic diagnostic apparatus 10A, the wireless communication unit 34 in the ultrasonic diagnostic apparatus 10 shown in FIG. 2 is replaced with an authentication wireless unit 60. The authentication wireless unit 60 corresponds to the wireless relay device 12 shown in FIGS. 1 and 2 incorporated in the ultrasonic diagnostic apparatus 10A, and has an authentication function for the communicator ID and the security information.

Before the authentication wireless unit 60 starts communication with the information terminal 14, the following communication connection processing is performed.

For example, the wireless security setting unit 36 reads a communicator ID from the connection information storage unit 38, and acquires from the control unit 30 the security information read from the operation unit 32 to the control unit 30. The wireless security setting unit 36 sets the communicator ID and the security information for the authentication wireless unit 60.

Next, processing executed by the information terminal 14 for the authentication wireless unit 60 will be described. The terminal user is notified of the communicator ID of the ultrasonic diagnostic apparatus 10A (authentication wireless unit 60) and the affiliated group ID by a research organization to which the terminal user belongs. The terminal user inputs the communicator ID and the affiliated group ID to the information terminal 14. The information terminal 14 reads the communicator ID and the affiliated group ID according to an operation of the terminal user, and sets the communicator ID and the affiliated group ID as the collation communicator ID and the collation security information, respectively. The information terminal 14 transmits a collation signal including the collation communicator ID and the collation security information to the authentication wireless unit 60.

The authentication wireless unit 60 receives the collation signal and extracts the collation communicator ID and the collation security information (affiliated group ID) from the collation signal. The authentication wireless unit 60 determines whether the collation communicator ID and the collation security information (affiliated group ID) match the communicator ID and the security information (shared group ID) set in the authentication wireless unit 60, respectively. When the collation communicator ID and the collation security information (affiliated group ID) match the communicator ID and the security information (shared group ID), respectively, the authentication wireless unit 60 establishes wireless communication with the information terminal 14.

When the collation communicator ID does not match the communicator ID or the collation security information (affiliated group ID) does not match the security information (shared group ID), the authentication wireless unit 60 does not establish wireless communication with the information terminal 14.

Figure 8:
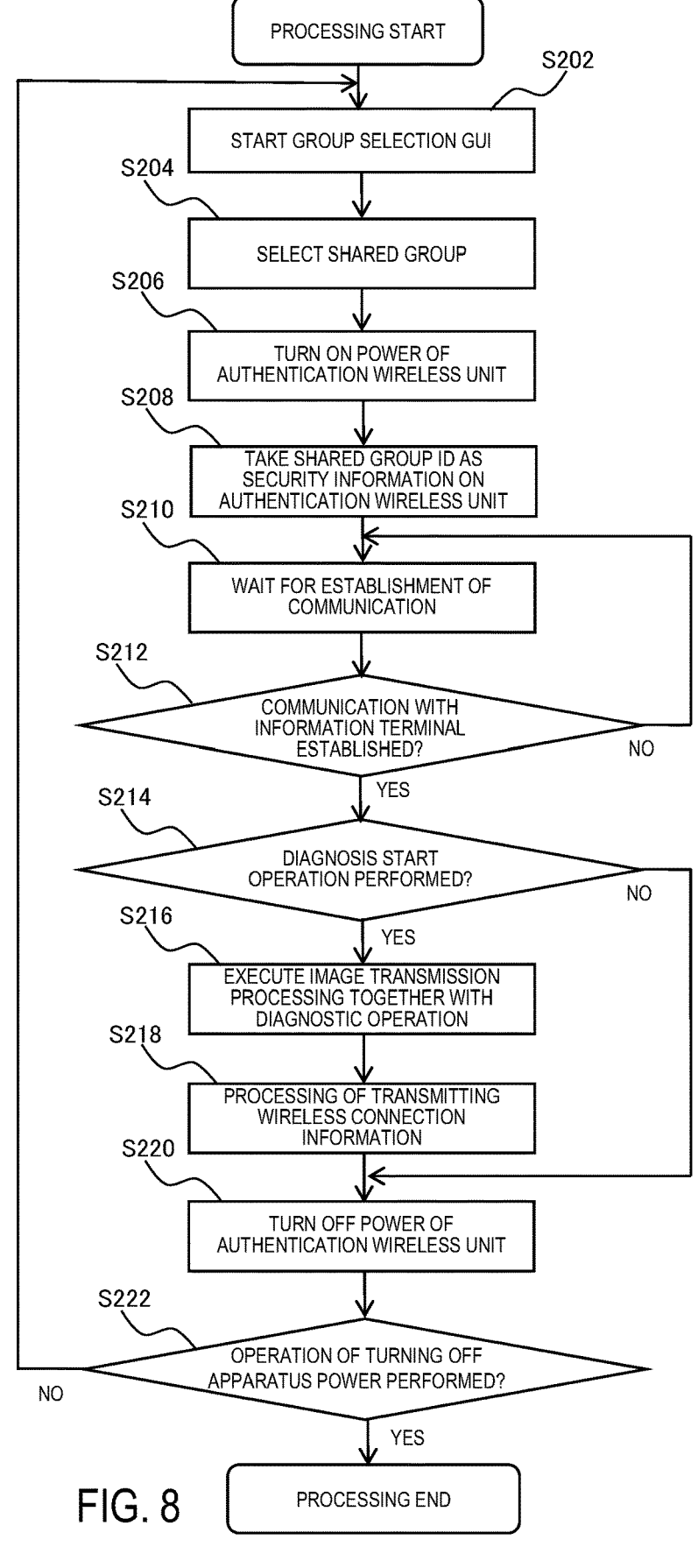
FIG. 8 is a flowchart of processing executed by the ultrasonic diagnostic apparatus according to the second embodiment.

An operation example of the ultrasonic diagnostic apparatus 10A will be described. FIG. 8 shows a flowchart of processing executed by the ultrasonic diagnostic apparatus 10A according to the present embodiment. In an initial state, power of the ultrasonic diagnostic apparatus 10A is on, but power of the authentication wireless unit 60 is off. A certain code is set as the communicator ID in the authentication wireless unit 60.

In accordance with an operation of the operation unit 32 by the diagnostic apparatus user, the control unit 30 starts a group selection GUI (S202). When the operation image is displayed on the display unit 28, the user selects a shared group (S204). As in the first embodiment, the operation image may be an image as shown in FIG. 4. The control unit 30 turns on the power of the authentication wireless unit 60 (S206), and outputs the shared group ID to the wireless security setting unit 36. The wireless security setting unit 36 takes the shared group ID as the security information on the authentication wireless unit 60 (S208). Accordingly, the authentication wireless unit 60 enters a state of waiting for establishment of communication with the information terminal 14 (S210).

The control unit 30 determines whether communication between the authentication wireless unit 60 and the information terminal 14 is established (S212), and waits for establishment of the communication between the authentication wireless unit 60 and the information terminal 14 when the communication is not established (S210).

When it is determined that the communication between the authentication wireless unit 60 and the information terminal 14 is established, the control unit 30 determines whether a diagnosis start operation is performed (S214). The control unit 30 starts a diagnostic operation when the diagnosis start operation is performed (S216), and proceeds to the processing of step S220 to be described later when the diagnosis start operation is not performed.

The control unit 30 executes image transmission processing together with the diagnostic operation (S216), and executes connection information transmission processing (S218). The information terminal 14 receives ultrasonic image information and the wireless connection information, and displays an ultrasonic image based on the ultrasonic image information and the wireless connection information.

Thus, the control unit 30 executes the group selection processing of selecting the shared group ID (S202, S204), when the affiliated group ID in the collation signal transmitted from the information terminal 14 to the authentication wireless unit 60 matches the shared group ID, executes the image transmission processing together with the authentication wireless unit 60 (S216), and executes the connection information transmission processing (S218).

The control unit 30 may, together with the authentication wireless unit 60, perform wireless communication with the plurality of information terminals 14 which transmit the same affiliated group ID to the authentication wireless unit 60. In this case, the control unit 30, together with the authentication wireless unit 60, executes the image transmission processing for the plurality of information terminals 14 (S216), and executes the connection information transmission processing (S218).

The image transmission processing and the connection information transmission processing may be performed by a conference system similar to that of the first embodiment. However, the present embodiment is different from the first embodiment in that the information terminal 14 and the ultrasonic diagnostic apparatus 10A perform direct wireless communication without using the communication line 16. The information terminal 14 which starts the conference system may display an image and information similar to the ultrasonic image 44 and the wireless connection information 46 shown in FIG. 5.

After the diagnostic operation ends and the image transmission processing and the connection information transmission processing is executed, the control unit 30 turns off the power of the authentication wireless unit 60 (S220). The control unit 30 determines whether an operation of turning off the power (apparatus power) of the ultrasonic diagnostic apparatus 10A is performed (S222). When the operation of turning off the apparatus power is not performed, the control unit 30 returns to the processing of step S202. When the operation of turning off the apparatus power is performed, the control unit 30 ends the processing.

In step S202, the control unit 30 starts the group selection GUI again. In response to an operation of the operation unit 32 by the diagnostic apparatus user, the control unit 30 selects a next shared group ID (S204). In processing in step S202 and following steps, a similar operation to the processing executed for the previous shared group ID is also executed for the next shared group ID.

According to the processing of step S208, the shared group ID is set as the security information on the authentication wireless unit 60. Therefore, the authentication wireless unit 60 establishes wireless communication with the information terminal 14 which transmits the collation signal, including the affiliated group ID that is the same as the shared group, ID as the collation security information. The affiliated group ID as the collation security information is read into the information terminal 14 by an operation of a terminal user. Therefore, the ultrasonic image information and the wireless connection information are transmitted to the information terminal 14 possessed by the terminal user who knows the affiliated group ID thereof. Further, the shared group ID is updated every time selection is performed in step S204. Therefore, unauthorized access by a person who is not related to a registered group selected as the shared group is avoided, and confidentiality when transmitting ultrasonic image information and the wireless connection information from the ultrasonic diagnostic apparatus 10 to the information terminal 14 is enhanced.

The power of the authentication wireless unit 60 is turned on while the processing for one selection of the shared group (S206 to S218) is executed, and is turned off from when the processing for one selection of the shared group ends to when a next shared group is selected. Accordingly, the possibility of unauthorized access to the ultrasonic diagnostic apparatus 10A is reduced.

In the processing shown in FIG. 8, a shared group is selected from a plurality of registered groups by an operation of the diagnostic apparatus user, and security information is set in the shared group ID. In addition to such processing, the ultrasonic diagnostic apparatus 10A may execute processing of setting the communicator ID of the ultrasonic diagnostic apparatus 10A (authentication wireless unit 60) by an operation of the diagnostic apparatus user. In this case, the control unit 30 reads the communicator ID from the operation unit 32 according to the operation of the diagnostic apparatus user. The control unit 30 outputs the communicator ID and the shared group ID to the wireless security setting unit 36. The wireless security setting unit 36 sets the communicator ID of the authentication wireless unit 60 and sets the security information as the shared group ID.

The terminal user is notified of the communicator ID and the affiliated group ID by a research organization to which the terminal user belongs. The terminal user inputs the communicator ID and the affiliated group ID to the information terminal 14. The information terminal 14 reads the communicator ID and the affiliated group ID according to an operation of the terminal user, and sets the communicator ID and the affiliated group ID as the collation communicator ID and the collation security information, respectively.

The information terminal 14 transmits a collation signal including the collation communicator ID and the collation security information (affiliated group ID) to the authentication wireless unit 60. When the collation communicator ID and the collation security information (affiliated group ID) match the communicator ID and the security information (shared group ID) set by the ultrasonic diagnostic apparatus 10A, respectively, the authentication wireless unit 60 establishes wireless communication with the information terminal 14.

According to such processing, not only the shared group ID but also the communicator ID is changed as needed, rather than being unchanged information. Accordingly, confidentiality when transmitting the ultrasonic image information and the wireless connection information to the information terminal 14 is enhanced.

In the above description, the embodiments are shown in which the ultrasonic diagnostic apparatus 10A performs direct wireless communication with the information terminal 14. Communication between the ultrasonic diagnostic apparatus 10A and the information terminal 14 may be performed via a wireless relay device which does not perform authentication or a wireless relay device which performs authentication different from authentication using the communicator ID and the security information.

The invention claimed is:

1. An ultrasonic diagnostic apparatus connected to a communication line via a wireless relay device and configured to communicate with an information terminal via the communication line and to transmit ultrasonic image information to the information terminal, the ultrasonic diagnostic apparatus comprising a processor configured by one or more programs of instructions to perform a method including steps comprising:

performing group selection processing of selecting, in response to a selection operation by a user of the ultrasonic diagnostic apparatus, a shared group ID, which is one of a plurality of registered group IDs registered in advance;

transmitting the shared group ID to the wireless relay device, only member devices associated with a group specified by the shared group ID being permitted to communicate through the wireless relay device with the ultrasonic diagnostic apparatus; and permitting, after the wireless relay device receives an affiliated group ID from the information terminal and determines that the affiliated group ID matches the shared group ID, wireless communication to be established between the ultrasonic diagnostic apparatus and the information terminal, and the ultrasonic image information to be transmitted to the information terminal.

2. The ultrasonic diagnostic apparatus according to claim 1, wherein the method performed by the processor further comprises:

communicating via the communication line with a plurality of information terminals which transmit the same affiliated group ID to the wireless relay device.

3. The ultrasonic diagnostic apparatus according to claim 1, wherein the method performed by the processor further comprises:

determining whether the information terminal, for which the affiliated group ID not matching the shared group ID is received by the wireless relay device, is an unauthorized access wireless terminal based on a communication operation of the information terminal.

4. The ultrasonic diagnostic apparatus according to claim 2, wherein the method performed by the processor further comprises:

determining whether the information terminal, for which the affiliated group ID not matching the shared group ID is received by the wireless relay device, is an unauthorized access wireless terminal based on a communication operation of the information terminal.

5. An ultrasonic diagnostic apparatus configured to perform wireless communication with an information terminal and transmit ultrasonic image information to the information terminal, the ultrasonic diagnostic apparatus comprising a processor configured by one or more programs of instructions to perform a method including steps comprising:

performing group selection processing of selecting, in response to a selection operation by a user of the ultrasonic diagnostic apparatus, a shared group ID, which is one of a plurality of registered group IDs registered in advance;

receiving an affiliated group ID from the information terminal; and comparing the affiliated group ID with the shared group ID, and when the affiliated group ID matches the shared group ID, performing wireless communication by the ultrasonic diagnostic apparatus with the information terminal, to transmit the ultrasonic image information to the information terminal.

6. The ultrasonic diagnostic apparatus according to claim 5, wherein the method performed by the processor further comprises:

performing wireless communication with a plurality of information terminals for which the same affiliated group ID is received.

7. The ultrasonic diagnostic apparatus according to claim 5, wherein the method performed by the processor further comprises:

determining whether the information terminal, for which the affiliated group ID not matching the shared group ID is received, is an unauthorized access wireless terminal based on a communication operation of the information terminal.

8. The ultrasonic diagnostic apparatus according to claim 6, the method performed by the processor further comprises:

determining whether the information terminal, for which the affiliated group ID not matching the shared group ID is received, is an unauthorized access wireless terminal based on a communication operation of the information terminal.

* * * * *